United States Patent [19]

Agouridas et al.

[11] Patent Number: 5,760,233
[45] Date of Patent: Jun. 2, 1998

[54] PROPANAL DERIVATIVES

[75] Inventors: Constantin Agouridas, Nogent sur Maine; Yannick Benedetti, Rosny sous Bois; Jean-Francois Chantot, Nogent sur Maine; Alexis Denis; Odile Le Martret, both of Paris, all of France

[73] Assignee: Roussel Uclaf, France

[21] Appl. No.: 805,439

[22] Filed: Feb. 25, 1997

Related U.S. Application Data

[62] Division of Ser. No. 414,503, Mar. 31, 1995, Pat. No. 5,656,607.

[30] Foreign Application Priority Data

Apr. 8, 1994 [FR] France .................... 94 04154

[51] Int. Cl.$^6$ .................... C07D 215/00; C07D 271/00; C07D 277/04; C07C 13/00
[52] U.S. Cl. .................... 546/152; 548/131; 548/146; 548/335.1; 585/24
[58] Field of Search .................... 546/152; 548/131, 548/146, 335.1; 585/24

[56] References Cited

U.S. PATENT DOCUMENTS 3,868,414   2/1975   Shen et al. .................... 556/17.2

*Primary Examiner*—Elli Peselev
*Attorney, Agent, or Firm*—Bierman, Muserlian and Lucas

[57] ABSTRACT

A compound selected from the group consisting of a compound of the formula

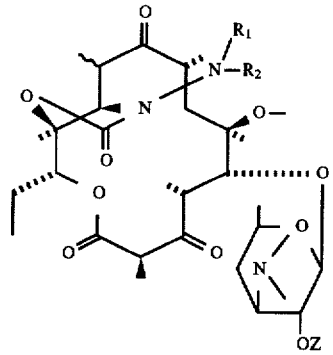

wherein $R_1$ and $R_2$ are individually selected from the group consisting of hydrogen and an optionally unsaturated hydrocarbon of up to 24 carbon atoms optionally interrupted by at least one heteroatom selected from the group consisting of oxygen, sulfur and nitrogen and optionally having at least one functional group or taken together form

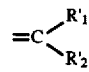

and $R'_1$ and $R'_2$ are individually selected from the group consisting of hydrogen and an optionally unsaturated hydrocarbon of up to 23 carbon atoms optionally interrupted by at least one heteroatom selected from the group consisting of nitrogen, oxygen and sulfur and optionally having at least one functional group. Z is hydrogen or acyl of an organic carboxylic acid of 1 to 18 carbon atoms and the wavy line indicates the 10-methyl may have R or S configuration or a mixture of R+S and their non-toxic, pharmaceutically acceptable acid addition salts having antibiotic properties.

1 Claim, No Drawings

5,760,233

1

PROPANAL DERIVATIVES

PRIOR APPLICATION

This application is a division of U.S. patent application Ser. No. 414,503 filed Mar. 31, 1995, now U.S. Pat. No. 5,656,607.

OBJECTS OF THE INVENTION

It is an object of the invention to provide the novel erythromycin derivatives of formula I and their non-toxic, pharmaceutically acceptable acid addition salts and a process for their preparation.

It is another object of the invention to provide novel antibiotic compositions and a method of combatting bacterial infections in warm-blooded animals.

These and other objects and advantages of the invention will become obvious from the following detailed descriptions.

THE INVENTION

The novel erythromycins of the invention are selected from the group consisting of a compound of the formula

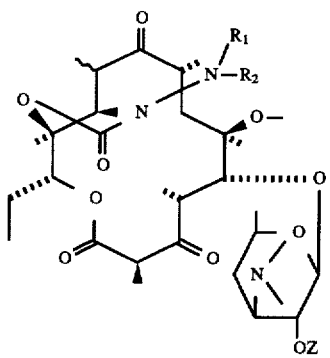

I wherein $R_1$ and $R_2$ are individually selected from the group consisting of hydrogen and an optionally unsaturated hydrocarbon of up to 24 carbon atoms optionally interrupted by at least one heteroatom selected from the group consisting of oxygen, sulfur and nitrogen and optionally having at least one functional group or taken together from

and $R'_1$ and $R'_2$ are individually selected from the group consisting of hydrogen and an optionally unsaturated hydrocarbon of up to 23 carbon atoms optionally interrupted by at least one heteroatom selected from the group consisting of nitrogen, oxygen and sulfur and optionally having at least one functional group, Z is hydrogen or acyl of an organic carboxylic acid of 1 to 18 carbon atoms and the wavy line indicates the 10-methyl may have R or S configuration or a mixture of R+S and their non-toxic, pharmaceutically acceptable acid addition salts.

Examples of suitable acids for the non-toxic, pharmaceutically acceptable acid addition salts are acetic acid, propionic acid, trifluoroacetic acid, maleic acid, tartaric acid, methane-sulfonic acid, benzenesulfonic acid, p-toluenesulfonic and particularly stearic acid, ethylsuccinic acid or laurylsulfonic acid.

Examples of hydrocarbons of $R_1$ or $R_2$ and $R'_1$ or $R'_2$ which can be interrupted by one or more heteroatoms

2 selected from nitrogen, oxygen and sulfur and can be substituted by at least one member of the group consisting of hydroxyl, halogen, —$NO_2$, —C≡N are alkyl, alkenyl or alkynyl, O-alkyl, O-alkenyl or O-alkynyl, S-alkyl, S-alkenyl or S-alkynyl and N-alkyl, N-alkenyl or N-alkynyl containing up to 12 carbon atoms optionally substituted by at least one halogen or

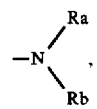

Ra and Rb, individually being selected from the group consisting of hydrogen, alkyl of up to 12 carbon atoms,

$R_3$ being alkyl of up to 12 carbon atoms, or an optionally substituted aryl or heteroaryl, carbocylic aryl, O-aryl or S-aryl or hetero- cyclic aryl, O-aryl or S-aryl with 5 or 6 ring members containing one or more heteroatoms, optionally substituted by one or more of the substituents mentioned above.

Examples of hydrocarbons of $R_1$ or $R_2$ and $R'_1$ or $R'_2$ are alkyl, alkenyl, alkynyl, aralkyl, aralkenyl or aralkynyl. Specific examples of the alkyl, alkenyl or alkynyl substituents are preferably methyl, ethyl, propyl, isopropyl, n-butyl, isobutyl, terbutyl, decyl, dodecyl, vinyl, allyl, ethynyl, propynyl, propargyl, cyclobutyl, cyclopentyl and cyclohexyl.

The aryl can be phenyl or naphthyl as well as a substituted or non-substituted heterocyclic such as thienyl, furyl, pyrolyl, thiazolyl, oxazolyl, imidazolyl, thiadiazolyl, pyrazolyl, isopyrazolyl, pyridyl, pyrimidyl, pyridazinyl or pyrazinyl or indolyl, benzofurannyl, benzothiazyl or quinolinyl. These aryl radicals can contain one or more of the above-mentioned substituents.

When $R_1$ and $R_2$ form with the nitrogen atom to which they are attached a heterocyclic, examples include pyrrolyl, pyrrolidinyl, pyridyl, pyrazinyl, pyrimidyl, piperidinyl, piperazinyl, quinuclidinyl, oxazolyl, isoxazolyl, morpholinyl, indolyl, imidazolyl, benzimidazolyl, triazolyl, thiazolyl, azetidinyl and aziridinyl.

Among the preferred compounds of formula I are those where Z is hydrogen, those wherein $R_1$ is hydrogen, those wherein $R_1$ and R form =CH—$(CH_2)_n$—$Ar_1$, wherein n is an integer from 0 to 8 and $Ar_1$ is optionally substituted aryl and optionally substituted heteroaryl, those wherein $R_1$ and $R_2$ form

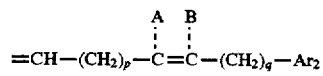

wherein p and q are individually integers from 0 to 6, A and B form a third bond between the carbons they are attached to or A and B individually are hydrogen or halogen or alkyl of 1 to 8 carbon atoms, the double bond having E or Z or E+Z geometry and $Ar_2$ is optionally substituted monocyclic or polycyclic aryl or heteroaryl and those wherein $R_2$ is —$(CH_2)_r$—$Ar_3$ wherein r is an integer from 0 to 6 and $Ar_3$ is optionally substituted aryl or heterocyclic.

$Ar_1$ is one of the preferred group above with the above optional substituents, p and q are preferably 0 and A and B are preferably hydrogen, r is preferably an integer from 1 to 4 and Ar₃ is preferably 4-quinolinyl optionally mono- or polysubstituted on the two rings such as 4-quinolinyl, 4-quinolinyl substituted with methoxy and thiazolyl substituted with pyridyl.

Specific preferred compounds of formula I are 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-(2-(3-(4-quinolinyl)-propyl)hydrazono)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-(2-(3-(7-methoxy-4-quinolinyl)-propyl)-hydrazono) ]-erythromycin and 11,12-dideoxy-3-de-[(2,6-dideoxy-3-C-methyl -3-O-methyl-α-L-ribohexopyranosyl)-oxy)-6-O-methyl-3-oxo-12,11-(oxycarbonyl-(2-(3-(2-(3-pyridinyl)-4-thiazolyl)-propyl)hydrazono)]-erythromycin and their acid addition salts.

The process of the invention for the preparation of a compound of formula I comprises reacting a compound of the formula

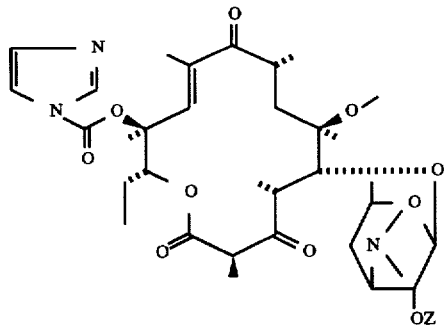

II wherein Z is defined as above either with hydrazine NH₂NH₂ to obtain a compound of the formula

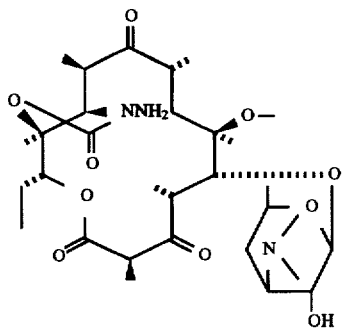

Iₐ optionally reacting the latter with R'₂CHO or

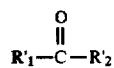

wherein R'₁ and R'₂ are defined as above to obtain a corresponding compound of the formula

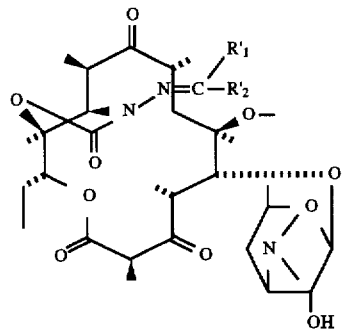

I_B wherein R'₁ and R'₂ are defined as above and optionally reacting the latter with a reducing agent to obtain a corresponding compound of the formula

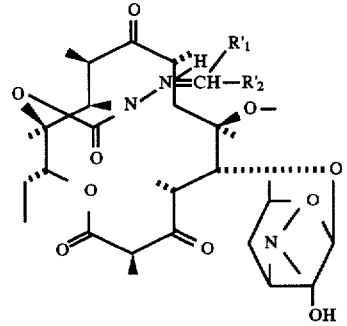

I_C wherein R'₁ and R'₂ are defined as above which is a compound of formula I in which $R_1$ is hydrogen and $R_2$ is CHR'₁R'₂ and optionally reacting the compound of formula I_C with an agent capable of replacing the hydrogen of NH group by an $R_1$ as defined above with the exception of the hydrogen value, and optionally the compound obtained is reacted with an acid to form the acid addition salt and/or with an esterification agent of the 2'-OH.

The compounds of formula II used as starting products of the process of the invention are described and claimed in European Patent Application EP 0,596,802 and are described in the Examples herein.

In a preferred embodiment of the process, the operation is carried out in the presence of an excess of hydrazine at a temperature greater than ambient temperature such as between 40 and 80° C. in a solvent such as acetonitrile, dioxane, dimethylformamide, tetrahydrofuran, dimethoxy ethane or dimethylsulfoxide in the presence or in the absence of a base, the reaction with the aldehyde or the ketone takes place under the same temperature and solvent conditions, the reducing agent is NaBH₃CN or hydrogen in the presence of a catalyst such as palladium or platinum and either in the presence or in the absence of an acid such as hydrochloric acid or acetic acid, the esterification in position 2' is carried out by standard processes and salification is carried by using acids by standard processes.

Also a variant of the preceding process comprises reacting the compound of the formula

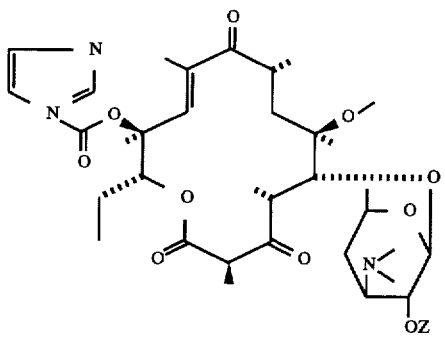

in which Z is as defined above with a compound of the formula $NH_2NHR_2$ to obtain a compound of the formula

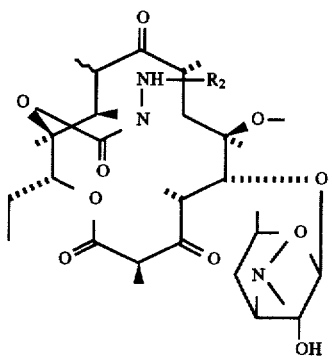

$I_A$ optionally reacting the latter with an agent capable of replacing hydrogen of the NH with $R_1$ as defined previously with the exception of hydrogen to obtain the corresponding compound of the formula

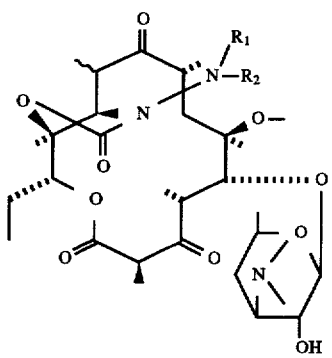

$I_B$ and optionally reacting the latter with an esterification agent of 2'- OH or with an acid to form the acid addition salt, the preferred temperature and pressure conditions being as described above.

The novel antibiotic compositions of the invention are comprised of an antibiotically effective amount of a compound of formula I or its non-toxic, pharmaceutically acceptable acid addition salts and an inert pharmaceutical carrier. The compositions may be in the form of tablets, dragees, capsules, granules, suppositories, ointments, creams, gels or injectable solution or suspensions.

Examples of suitable carrier are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The compositions of the invention possess a very good antibiotic activity on gram bacteria such as staphylococci, streptococci and pneumococci and can therefore be used as medicaments in the treatment of infections caused by sensitive germs, especially that of staphylococcia such as staphylococcal septicemias, malignant staphylococcia of the face or skin, pyodermatitis, septic or suppurating sores, boils, anthrax, phlegmons, erysipelas and acne, staphylococcia such as primary or post-influenzal acute anginas, bronchopneumonia, pulmonary suppuration, streptococcal infection such as acute anginas, otitis, sinusitis, scarlet fever, pneumococcal infection such as pneumonia, bronchitis; brucellosis, diphtheria and gonococcal infection.

The compositions of the present invention are also active against infections caused by germs such as Haemophilus influenzae, Rickettsia, Mycoplasma pneumoniae, Chlamydia, Legionella, Ureaplasma, Toxoplasma, or by germs of Mycobacterium type.

The method of the invention for treating bacterial infections in warm-blooded animals, including humans, comprises administering to warm-blooded animals an antibiotically effective amount of a compound of formula I or it non-toxic, pharmaceutically acceptable acid addition salts. The compounds may be administered orally, rectally, parentally or topically by application to the skin or mucous membranes. The usual daily dose is 0.6 to 4 mg/kg depending on the condition treated, the method of administration and the specific compound used.

In the following examples, there are described several preferred embodiments to illustrate the invention. However, it should be understood that the invention is not intended to be limited to the specific embodiments.

EXAMPLE 1

11,12-dideoxy-3-de-((2,6-dideoxy-3-C-methyl-3-O-methyl-α-L-ribohexopyranosyl)-oxy)-6-O-methyl-3-oxo-12,11-(oxycarbonyl(hydrazono)-erythromycin isomer 10(R) and corresponding isomer 10(S)

353 mg of 11-deoxy-10,11-didehydro-3-de-(2,6-dideoxy-3-C-methyl-3-O-methyl-α-L-ribohexopyranosyl)-oxy)-12-O-((1H-imidazol-1-yl)-carbonyl)-6-O-methyl-3-oxo-erythromycin-2'-acetate [prepared in European Patent Application EP 0,596,802] and 0.097 ml of hydrazine hydrate were suspended in 5 ml of methyl cyanide and 0.5 ml of water and the reaction mixture was heated to 60° C. for 3 hours. The reaction mixture was poured into water and extraction was carried out with ethyl acetate. The extracts were washed and dried. The reaction mixture was chromatographed on silica and eluted with an isopropyl ether, triethylamine, methanol mixture (90/10/10) to obtain 101 mg of the desired product (product A), with a $R_f$=0.45, and 106 mg of the corresponding product 10(S) (product B).

| Product A: | | | |
|---|---|---|---|
| | | found | |
| Analysis | calculated | Pdt (A) | Pdt (B) |
| % C | 59.31 | 59.3 | 59.3 |
| % H | 8.51 | 8.4 | 8.4 |
| % N | 6.69 | 6.7 | 6.8 |

| Product A: NMR CDCl$_3$ ppm | | Product B: NMR CDCl$_3$ ppm | |
|---|---|---|---|
| 3.09 | $H_{10}$ (m) | 3.53 | $H_{10}$ (m) |
| 3.59 | $H_{11}$ (s) | 3.46 (d, J=3Hz) | $H_{11}$ (s) |
| 1.35 | 12 Me (s) | 1.32 | 12 Me (s) |

| | | | |
|---|---|---|---|
| 5.03 | $H_{13}$ (dd) | 4.95 | $H_{13}$ (dd) |
| 0.86 | 15 Me (t) | 0.87 | 15 Me (t) |
| 3.85 | $H_2$ (q) | 3.88 | $H_2$ (q) |
| 2.30 | N—Me (s) | 2.31 | N—Me (s) |
| 2.67-6 | OMe (s) | 2.83 | 6-OMe (s) |
| 4.44 | NH (s) | 3.84 | NH (s) |
| 2.67 | $H_8$ (m) | 2.78 | $H_8$ (m) |

EXAMPLE 2

11,12-dideoxy-3-de-(2,6-dideoxy-3-C-methyl-3-O-methyl-α-L-ribohexopyranosyl)-oxy)-6-O-methyl-3-oxo-12,11-(oxycarbonyl-(2-(3-phenylpropylidene)-hydrazono))-erythromycin 285 mg of product A of Example 1 and 156 mg of 3-phenylpropionaldehyde were dissolved in 2 ml of THF with a molecular sieve (4A°). 100 mg of a molecular sieve (4A°) were added and the mixture was heated at 60° C. for 24 hours. Filtration was carried out, followed by concentration and purification by chromatography on silica, eluting with an ethyl acetate-triethylamine mixture (96-4). The fractions of $R_f$=0.41 were collected to obtain 330 mg of the desired product with a $R_f$=0.3.

| Analysis | calculated | found |
|---|---|---|
| % C | 64.58 | 64.3 |
| % H | 8.26 | 8.3 |
| % N | 5.65 | 5.5 |
| NMR $CDCl_3$ ppm | | |
| 3.04 | $H_{10}$ (q) | |
| 4.46 | $H_{11}$ (d, j = 3 Hz) | |
| 5.05 | $H_{13}$ (dd) | |
| 3.85 | $H_2$ (q) | |
| 2.38 | NMe (s) | |
| 2.79 | 6 OMe (s) | |
| 7.96 | N=CH (t) | |
| 2.86 | $CH_2$-Φ | |
| 7.2, 7.35 | H aromatics | |
| 2.61 | NH=CH—$CH_2$ (m). | |

EXAMPLE 3

11,12-dideoxy-3-de-[(2,6-dideoxy-3-C-methyl-3-O-methyl-α-L-ribohexopyranosyl)-oxy)-6-o-methyl-3-oxo-12,11-(oxycarbonyl-(2-(3-phenylpropyl)-hydrazono)]-erythromycin 23 mg of sodium cyanoborohydride ($NaBH_3CN$) were added to a solution of 1.5 ml of methanol, 88 mg of the product of Example 2 and 50 μl of acetic acid. After concentration and taking up in ethyl acetate, water was added and the pH was adjusted to 8 using a solution of 2N sodium hydroxide. Decanting was carried out, followed by washing with a saturated solution of sodium chloride and drying. The product was chromatographed on silica and eluted with an isopopyl ether-methanol-triethylamine mixture (90-10-10). The fractions of $R_f$=0.33 were collected and the mixture obtained was taken up in an ether-pentane mixture and filtered. After evaporation, 70 mg of the expected product were obtained.

| Analysis | calculated | found |
|---|---|---|
| % C | 64.4 | 64.2 |
| % H | 8.51 | 8.3 |
| % N | 5.63 | 5.6 |
| NMR $CDCl_3$ ppm | | |
| 3.74 | $H_{10}$ (s) | |
| 5.03 | $H_{13}$ (dd) | |
| 3.86 | $H_2$ (q) | |
| 2.27 | $N(CH_3)_2$ (s) | |
| 2.64 | 6 OMe (s) | |
| 2.72 | $CH_2$-Φ | |
| 7.13-7.28 | H aromatics | |
| 5.35 | H of NH (t). | |

EXAMPLE 4

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-(2-(3-(4-quinolinyl)-2(E)-propenylidene)-hydrazono)]-erythromycin 125 mg of product A of Example 1, 73 mg of 4-quinolinylpropenal and 40 μl of acetic acid were stirred at ambient temperature for 5 hours. The methanol was eliminated under reduced pressure and the residue was taken up in a methylene chloride-water mixture. The pH was adjusted to 9 using a concentrated ammonium hydroxide solution. The reaction medium was decanted, dried over magnesium sulfate, filtered and evaporated to dryness to obtain 0.211 g of a product which was chromatographed on silica and eluted with a methylene chloride-methanol mixture (92-8). The product of $R_f$=0.4 was impasted in an ethyl acetate-pentane mixture (1-1). After separating and rinsing with the minimum amount of ethyl acetate-pentane mixture, the product was oven-dried under reduced pressure to obtain 109 mg of the desired product.

PREPARATION OF EXAMPLE 4: 4-quinoline-propenal 3.9 g of 4-quinoline carboxaldehyde were dissolved in 80 ml of methylene chloride. The mixture was cooled to 10° C.±5° C. and 8.3 g of 3-(triphenylphosphine)-propenal $(C_6H_5)_3P=C$—CHO were added over 90 minutes while maintaining the temperature at 10° C. The temperature was allowed to return to 20° C. and stirring was continued for 24 hours. The reaction medium was cooled again to 10° C. and 0.4 g of $(C_6H_5)_3P=C$—CHO were added. The mixture was stirred for 3 hours at ambient temperature and the methylene chloride was evaporated off to obtain a residue which was chromatographed on silica and eluted with an ethyl acetate-cyclohexane mixture (4-6) to obtain 2.12 g of the desired product melting at approximately 90° C.

EXAMPLE 5

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-(2-(3-(4-quinolinyl)-2-propyl)-hydrazono)]-erythromycin 0.38 g of the product of Example 4 and 38 mg of platinum oxide were dissolved in 10 ml of ethyl acetate and hydrogenation was carried out with vigorous stirring for 24 hours. After filtration, rinsing with ethyl acetate and evaporating under reduced pressure, 0.375 g of product were obtained which was taken up in 5 ml of methanol, 175 μl of acetic acid and 90 mg of sodium borohydride. The mixture was stirred for 3 hours at ambient temperature. The methanol was evaporated and the residue was taken up in a methylene chloride-water mixture. The pH was adjusted to 8–9 with a 28% ammonium hydroxide solution. After decanting, washing with water, drying, filtering and evaporating to dryness, 0.37 g of product were obtained which was chromatographed on silica and eluted with an ethyl acetate-triethylamine mixture 96-4 to obtain 127 mg of a product with a $R_f=0.25$ which was separated, washed and dried to obtain 90 mg of the desired product melting at 189° C.

EXAMPLE 6

11 12-dideoxy-3-de-[(2,6-dideoxy-3-C-methyl-3-O-methyl-α-L-ribohexopyranosyl)-oxy)-6-O-methyl-3-oxo-12,11-(oxycarbonyl-(2-(3-(1H-benzimidazol-1-yl)-propyl)-hydrazono))]-erythromycin A solution of 0.3 g of the product of Example 1, 0.168 g of 3-imidazolyl-propanal and 90 ml of acetic acid in 9 ml of methanol was stirred for 18 hours at ambient temperature. After this, 40 mg of sodium cyanoborohydride were added and stirring was continued for 5 hours. Then, 120 mg of sodium cyanoborohydride and 200 μl of acetic acid were added and stirring was continued for 48 hours. A methylene chloride and water mixture was added and the pH was adjusted to 8–9 with 32% ammonium hydroxide. The organic phase was separated, dried and evaporated to dryness to obtain 0.6 g of residue which was chromatographed on silica (eluant: ethyl acetate-methanol-TEA: 92-6-2). The product was impasted in an 1-5 ether-pentane mixture. 0.143 g of the crude desired product were dissolved in 1 ml of ethyl acetate, followed by filtration and crystallization by the addition of 3 ml of pentane to obtain after drying, 0.085 g of the desired product melting at 197° C. Analysis: C$_{41}$H$_{63}$N$_5$O$_{10}$; molecular weight=785.98

|  | C | H | N |
|---|---|---|---|
| % calculated | 62.65 | 8.08 | 8.91 |
| % found | 62.5 | 8.1 | 8.8 |

NMR CDCl$_3$ ppm 3.18: H$_{10}$; 3.69 (s): H$_{11}$; 0.84 (t): 15 CH$_3$; 3.86 (q): H$_2$; 2.45: N—(OH$_3$)$_2$; 2.60 (s): 6 OCH$_3$; 5.56 (t): NH; 2.65–2.81: NH—C$\underline{H}_2$—; 4.50:

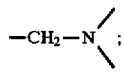

7.26 to 8.02: 5H benzimidazole.
PREPARATION OF: 3-imidazolyl-propanal
Stage A: 2-(2-(3-imidazolyl)-ethyl)-1,3-dioxolane 0.49 g of sodium hydride dispersed in oil at 50% were added to a solution of 1.2 g of benzimidazole in 15 ml of dimethylformamide. The temperature rose to 35° C. ten minutes after the end of the gaseous release and 1.2 ml of 2-(2-bromoethyl)-1,3-dioxolane were added while allowing the temperature to rise to 35° C. The mixture was stirred for two hours and water saturated with sodium chloride was added. Extraction was carried out with ether and the extracts were dried, filtered and evaporated under reduced pressure to obtain 2 g of residue which was chromatographed on silica eluting with methylene chloride-methanol (95-5) to obtain 1.6 g of the desired product.

NMR CDCl$_3$: 2.25 and 4.35: CH$_2$'s of the ethyl; 3.85 to 4.00: CH$_2$'s of the dioxolane; 4.87: CH dioxolane; 7.29–7.45–7.81: 4H benzimidazole; 7.92: H in position 2 of the imidazole.

STAGE B: 3-imidazolyl-propanal

A solution of 1.6 g of the product of Stage A, 1.45 g of p-toluene sulfonic acid in 60 ml of methanol was stirred for 5 hours at reflux and the pH was adjusted to 8 with potassium carbonate. The methanol was eliminated under reduced pressure and extraction was carried out with methylene chloride, followed by washing with water, drying and evaporating to dryness under reduced pressure to obtain 1.45 g of intermediate dimethoxy ketal which was stirred at 40° C. for 18 hours in the presence of 70 ml of acetone and 34 ml of 2N hydrochloric acid. The acetone was evaporated under reduced pressure and the pH was adjusted to 8–9 by the addition of 32% ammonium hydroxide. Extraction was carried out with methylene chloride and the extracts were washed with water, dried and evaporated to dryness under reduced pressure to obtain 1.13 g of product which was chromatographed on silica, eluant: methylene chloride-methanol 95-5 to obtain 0.796 g of the desired product.

NMR CDCl$_3$ 250 MHz 3.07 (t)–4.52 (t): CH$_2$'s of the ethyl; 7.25 to 7.50: the aromatics; 9.79 (s): CH of the aldehyde.

EXAMPLE 7

11,12-dideoxy-3-de-[(2,6-dideoxy-3-C-methyl-3-O-methyl-α-L-ribohexopyranosyl)-oxy)-6-o-methyl-3-oxo-12,11-(oxycarbonyl-(2-(3-(2-phenyl-5-thiazolyl)-propyl)-hydrazono))]-erythromycin 60 mg of sodium cyanoborohydride were added to a mixture of 200 mg of the product of Example 1, 139 mg of 3-(2-phenyl-5-thiazolyl)-propanal, 180 ml of acetic acid and 7 ml of methanol with stirring over 4 hours at ambient temperature and the mixture was stirred for 18 hours at ambiant temperature. Evaporation to dryness under reduced pressure was carried out and the residue was taken up in a water-ethyl acetate mixture. The pH was adjusted to 9 with an aqueous ammonium hydroxide solution and extraction carried out with ethyl acetate. The extracts were washed with water, dried and evaporated to dryness under reduced pressure to obtain 354 mg of product which was chromatographed on silica, eluant: ethyl acetate then ethyl acetate-triethylamine (96/4) to obtain 170 mg of product which was crystallized from an ethyl acetate-pentane mixture 1/5 to obtain 80 mg of the desired product.

Analysis: C$_{43}$H$_{64}$N$_4$O$_{10}$S; molecular weight=829.07

|  | C | H | N | S |
|---|---|---|---|---|
| % calculated | 62.3 | 7.78 | 6.76 | 3.87 |
| % found | 62.0 | 7.8 | 6.8 | 4.0 |

NMR CDCl$_3$ 300 MHz 3.17 (m): H$_{10}$; 1.07 (d): 14 CH$_3$; 1.48: 15 CH$_3$; 3.87 (q): H$_2$; 2.26 (s): N-(CH$_3$)$_2$; 3.53 (m): 2'OH; 2.67 (s) : 6-OCH$_3$; 5.43 (t): NH; 2.86 (m)-1.95 (m)-3.03 (m): the propyl CH$_2$'s; 7.55 (s): H of the thiazole; 7.39 (m) 3H and 7.89 (m) 2H: aromatics; 1.19 (d): H$_8$.
PREPARATION OF EXAMPLE 7: 2-phenyl-5-thiazole-propanal
Stave A: 2-phenyl-5-carbethoxy-thiazole A solution of ethyl formyl β chloracetate in 240 ml of benzene was added to a suspension of 78 g of thiobenzamide in 200 ml of benzene and the mixture was refluxed for 3 hours 30 minutes while eliminating the water formed. The reaction medium was cooled and 320 ml of a 20% solution of potassium carbonate and 220 ml of water were added slowly. Extraction was carried out with ether, followed by washing, drying and distillation under reduced pressure to obtain 75.5 g of the desired product.

Stave B: 2-phenyl-5-thiazole-carboxylic acid 28.56 g of potassium hydroxide in pellets in solution in 410 ml of ethanol were added to a solution of 75.5 g of the product of Stage A in 130 ml of ethanol. The mixture was heated for 15 minutes at reflux, cooled and the potassium salt was separated off, washed with ether and dried under reduced pressure to obtain 53.5 g of intermediate potassium salt which was dissolved in 1.2 liters of water and acidified to pH 1 with a concentrated hydrochloric acid solution. After filtration, 29 g of the desired product melting at 192° C. were obtained. 24.5 g of the product were crystallized from 750 ml of toluene to obtain 20 g of the desired product melting at 195° C.

Analysis: $C_{10}H_7NO_2S$; molecular weight=205.2

|  | C | H | N | S |
|---|---|---|---|---|
| % calculated | 58.52 | 3.43 | 6.82 | 15.6 |
| % found | 58.5 | 3.7 | 6.8 | 15.2 |

Stage C: methyl 2-phenyl-5-thiazole carboxylate 2.5 ml of acetyl chloride were added to a solution of 4.77 g of the acid of Stage B in 160 ml of methanol, and the mixture was refluxed for 18 hours. After evaporating to dryness under reduced pressure, the residue was taken up in ethyl acetate. The mixture was filtered and concentrated to a reduced volume. The crystals were separated off and the mother liquors were washed with sodium hydroxide. Extraction was carried out with ethyl acetate, followed by washing with water and evaporating to dryness. The 2 crystallized fractions were combined to obtain 4.54 g of the desired product melting at 108° C.

Stage D: 2-phenyl-5-formyl-thiazol
Reduction

A solution of 4.5 g of the product of Stage C in 35 ml of tetrahydrofuran was added over 20 minutes and while maintaining the temperature at 10° C. to a suspension of 1.45 g of lithium-aluminium hydride in 65 ml of tetrahydrofuran cooled to 10° C. The mixture was stirred for 45 minutes at 10° C., then for 2 hours at ambient temperature. Then, 50% tetrahydrofuran in water was added while maintaining the temperature below 20° C. and 15 ml of a solution of potassium sodium tartrate was added. Filtration was carried out followed by rinsing and bringing to dryness under reduced pressure. The residue was impasted in hexane, separated and dried at 40° C. under reduced pressure to obtain 3.6 g of the product melting at 82° C.

Oxidation 3.57 g of the product obtained above were stirred for 2 hours 30 minutes at ambient temperature with 143 ml of toluene and 17.9 g of manganese dioxide. After filtration and evaporating to dryness under reduced pressure, the residue was taken up in hexane, separated and dried at 40° C. under reduced pressure to obtain 3.09 g of the desired product melting at 94° C.

Stage E: 3-(2-phenyl-5-thiazolyl)-propenal 5 g of (formylmethylene) triphenylphosphorane were added over 10 minutes to a solution of 2.098 g of the product of Stage D, and the mixture was stirred for 27 hours at ambient temperature. After evaporating to dryness under reduced pressure, (6.60 g of product were chromatographed on silica eluting with ethyl acetate-cyclohexane (2-8) to obtain 1.22 g of product which was impasted in pentane to obtain 1.047 g of the desired product melting at 104° C.

NMR $CDCl_3$ (250 MHz) 8.04 (s): H triazole; 6.49 (ddJ= 7.5) and 7.69 (dJ=15.5) the propene H's; 9.67 (J=7.5) CHO; 7.50 (m) 3H and 7.97 (m) 2 H: the aromatics.

Stage F: 3-(2-phenyl-5-thiazolyl)-propenol 900 mg of the aldehyde of Stage E were added in portions to a suspension of 475 mg of sodium borohydride in 50 ml of ethanol and the mixture was stirred for 20 minutes at ambient temperature. Then, the excess sodium borohydride was destroyed by adding acetone. Evaporation to dryness under reduced pressure was carried out followed by taking up in ethyl acetate, washing with salt water, drying and evaporating to dryness under reduced pressure to obtain 960 mg of the desired product which was used as is for the following stage.

Stage G: 2-phenyl-5-thiazole-propanol

A solution of 960 mg of the product of Stage F in 10 ml of methanol was hydrogenated for 12 hours at one atmosphere, then for 9 hours under 1.4 atmospheres in the presence of 150 mg of palladium on charcoal. After filtration, evaporation to dryness under reduced pressure was carried out. The residue was chromatographed on silica (eluant: ethyl acetate-cyclohexane (4–6)) to obtain 759 mg of the desired product.

NMR $CDCl_3$ 200 MHz 1.52 (m): OH; 3.74 (m) –1.97 (m) –2.92 (dt): the $CH_2$'s; 7.40 to 7.90 (m): 5H aromatics; 7.53 (t, J=1): H thiazole.

Stage H: 2-phenyl-5-thiazole-propanal 1.27 g of pyridinium sulfotrioxide complex were added to a solution cooled to 10° C. of 584 mg of the product of Stage G, 800 µl of dimethylsulfoxide, 1.15 ml of triethylamine and 8 ml of methylene chloride while maintaining the temperature at 10° C. The mixture was stirred for 75 minutes at 10° C., then left to return to ambient temperature. Extraction was carried out with methylene chloride, followed by washing with water, drying and evaporating to dryness under reduced pressure to obtain 806 mg of product which was chromatographed on silica (eluant: ethyl acetate-cyclohexane (3–7)) to obtain 450 mg of the desired product.

NMR $CDCl_3$ 200 MHz 2.88–3.20 (t): the propyl $CH_2$'s; 7.55 (s): H thiazole; 7.40 (m): 3H and 7.87 (m) 2H: the aromatic H's; 9.85 (ws): CHO.

EXAMPLE 8

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-(2-(3-(4-phenyl-1H-imidazol-1-yl)-propyl)-hydrazono)]-erythromycin 125 mg of the product of Example 1, 80 mg of 3-(4-phenyl-1H-imidazole-1-yl)-propanal and 2 ml of methanol were stirred for 20 hours and then 54 mg of sodium cyanoborohydride were added. Concentration under reduced pressure was carried out and the residue was taken up in 20 ml of ethyl acetate, washed with sodium hydroxide, then with water saturated with sodium chloride, dried and evaporated to dryness under reduced pressure. The residue was chromatographed on silica (eluant: chloroform-methanol-ammonium hydroxide 95/5/0.5) and the crude product was taken up in an ether-ethyl acetate mixture, filtered and evaporated to dryness to obtain 85 mg of the desired product.

Analysis: $C_{43}H_{65}N_5O_{10}$; molecular weight=812.02

|  | C | H | N |
|---|---|---|---|
| % calculated | 63.6 | 8.07 | 8.62 |
| % found | 63.4 | 8.2 | 8.3 |

NMR $CDCl_3$ 400 MHz 3.70 (s): H in position 11; 4.98 (dd): $H_{13}$; 3.86 (q): H in position 2; 2.26 (s): N—$(CH_3)_2$;

2.63: 6-OCH$_3$; 5.54 (t): NH; 4.27 and 1.97: the propyl CH$_2$'s; 7.3 (d)–7.57 (d): 2H imidazole; 7.2 –7.35–7.8: the aromatics.

PREPARATION OF EXAMPLE 8: 3-(4-phenyl-1H-imidazol-1-yl)-propanal

Stage A : 3-(4-phenyl-1H-imidazol-i-yl)-ethyl-1,3-dioxolane

Using the procedure of Stage A of the preparation of Example 6, 1.44 g of 4-phenylimidazole and 1.17 ml of bromoethyldioxolane were reacted to obtain after chromatography on silica (eluant: ACOEt), 1.8 g of the expected product.

NMR CDCl$_3$ 2.19 (d,t) and 4.13 (t): propyl CH$_2$; 3.8–4.05: the CH 2's of dioxolane; 4.88 (t): H oxolane; 7.23 and 7.53: the imidazo:Le CH's; 7.23–7.37–7.75: the aromatics.

Stage B: 3-(4-phenyl-1H-imidazol-1-yl)-propanal 1.77 g of the product of Stage A, 35 ml of acetone and 30 ml of 2N hydrochloric acid were heated for 20 hours at 60° C. The acetone was eliminated under reduced pressure and the solution was neutralized by adding sodium bicarbonate in sticks. Then, extraction was carried out with ethyl acetate, followed by drying and evaporating to dryness under reduced pressure. The residue was chromatographed on silica (eluant: ethyl acetate-methanol (97-3)) to obtain 900 mg of the desired product.

NMR CDCl$_3$ 250 MHz 9.81 (s): CHO; 7.10 to 7.76: the imidazole and aromatic H's; 3.01 (t) and 4.29 (t): the propyl H's.

EXAMPLE 9

11,12-dideoxy-3-de-[(2,6-dideoxy-3-C-methyl-3-O-methyl α-L-ribohexopyranosyl)-oxy)-6-O-methyl-12,11-(oxycarbonyl-(2-(3-(3-phenyl-1,2,4-oxadiazol-5-yl)-propyl)-hydrazono)]-erythromycin Using the procedure of Example 6, 125 mg of the product of Example 1, 40 mg of 3-(3-phenyl-1,2,4-oxadiazol-5-yl)-propanal were reacted to obtain after chromatography on silica, eluant: isopropyl ether-triethylamine-methanol (90-10-10) and crystallization from isopropyl ether-methanol, 107 mg of the expected product.

Analysis: C$_{42}$H$_{63}$N$_5$O$_{11}$; molecular weight=814.00

|  | C | H | N |
|---|---|---|---|
| % calculated | 61.97 | 7.8 | 8.6 |
| % found | 61.7 | 7.9 | 8.5 |

NMR CDCl$_3$ 300 MHz 3.74 (s): H$_{11}$; 5.03 (dd): H$_{13}$; 3.87 (q): H$_2$; 2.27 (s): 6-OCH$_3$; 2.27 (s): N—(CH$_3$)$_2$; 5.49 (t): NH; 3.17 (m) and 2.11 (m): the propyl CH$_2$'s; 7.47 to 8.08: the aromatics.

PREPARATION OF EXAMPLE 9: 3-(3-phenyl-1,2,4-oxadiazol-5-yl)-propanal

Stage A: 3-(3-phenyl-1,2,4-oxadiazol-5-yl) propanol

A solution of 2.5 ml of borane-methyl sulfide complex in 2M solution in tetrahydrofuran, 920 mg of 3-(3-phenyl-1,2,4-oxadiazol 5-yl)-propanoic acid (prepared by SRIRASTAVA et al., J. Heterocycl. Chem., Vol. 21, p. 1193 (1984) and 20 ml of tetrahydrofuran was stirred for one hour at ambient temperature. 10 ml of methanol were added over 5 minutes and evaporation to dryness under reduced pressure was carried out. The residue was chromatographed on silica (eluant: ethyl acetate-hexane (6-4)) to obtain 485 mg of the expected product.

NMR CDCl$_3$ 250 MHz 2 .07 (ws): OH; 2.14 (m)–3.10 (t)–3.8 (t): the CH$_2$'s; 7.41–7.54–8.06: the aromatics.

Stage B: 3-(3-phenyl-1,2,4-oxadiazol-5-yl)-propanal 1.07 g of pyridinium sulfotrioxide complex were added to a solution cooled to 10° C. of 460 mg of the product of Stage A, 680 µl of dimethylsulfoxide and 970 µl of triethylamine in 5 ml of methylene chloride while maintaining the temperature at 10° C. The reaction medium was allowed to return to ambient temperature and 15 ml of methylene chloride were added, followed by washing with water, drying, evaporating to dryness under reduced pressure and chromatographing on silica (eluant: ethyl acetate-hexane 4-6) to obtain 365 mg of the desired product.

NMR CDCl$_3$ 3.13 (m)–3.26 (m): the CH$_2$'s; 7.49 to 8.05: the aromatics.

EXAMPLE 10

11,12-dideoxy-3-de-[(2,6-dideoxy-3-C-methyl-3-O-methyl α-L-ribohexopyranosyl)-oxy)-6-O-methyl-3-oxo-12,11-(oxycarbonyl-(2-(3-(2-chlorophenyl)-propyl)-hydrazono)]-erythromycin Using the procedure of Example 6, 125 mg of the product of Example 1 and 67 mg of 2-chlorophenyl-propanal were reacted to obtain after chromatography on silica (eluant: isopropyl ether-triethylamine-methanol (90-10-10)), 48 mg of the desired product.

Analysis: C$_{40}$H$_{62}$ClN$_3$O$_{10}$; molecular weight=780.40

|  | C | H | N | S |
|---|---|---|---|---|
| % calculated | 61.56 | 8.01 | 5.38 | 4.45 |
| % found | 61.4 | 8.0 | 5.4 | 4.5 |

NMR CDCl$_3$ 400 MHz 3.73 (s): H in position 11; 5.13 (dd): H in position 13; 3.87 (q): H in position 2; 2.26 (s) : N—(CH$_3$)$_2$; 2.64 (s): 6-OCH$_3$; 5.36 (t): NH; 1.83 (m)–2.70 (m)–2.79 (m): the CH$_2$'s; 7.05 to 7.2: the aromatics.

PREPARATION OF: 3-(2-chlorophenyl)-propanal

Stage A: methyl 3-(2-chlorophenyl)-propanoate 4.35 g of m-chlorocinamic acid, 430 mg of palladium on activated charcoal and 70 ml of methanol were stirred for one hour under an inert atmosphere and then for 3 hours under a hydrogen atmosphere. The reaction medium was filtered and evaporated to dryness under reduced pressure. The residue was chromatographed on silica (eluant: ethyl acetate-hexane (2-8)) to obtain 3.1 g of the desired product.

NMR CDCl$_3$ 250 MHz 2.6 (t)–2.8 (t): the CH$_2$'s; 3.6 (s): OCH$_3$; 7.05–7.37: the aromatics.

Stage B: 3-(2-chlorophenyl)-propanol 30 ml of diisobutylaluminium hydride in a 1M solution in tetrahydrofuran were added at 0° C. to a solution of 1.85 g of the product of Stage A in 20 ml of tetrahydrofuran and the mixture was allowed to return to ambient temperature and then was stirred for 2 hours. A solution of mixed sodium-potassium tartrate was added and dilution was carried out with tetrahydrofuran, followed by filtration and evaporation to dryness under reduced pressure. The residue was chromatographed on silica (eluant: ethyl acetate-hexane (2-8)) to obtain 1 g of the desired product was obtained.

Stage C: 3-(2-chlorophenyl)-propanal

Using the procedure of Stage B of Preparation 9, 1 g of the product of Stage B and 2.5 ml of triethylamine, 1.75 ml of dimethyl sulfoxide and 2.8 g of pyridinium sulfotrioxide complex were reacted to obtain after chromatography on silica, eluant: ethyl acetate-hexane (1-9), 425 mg (43%) of the desired product.

NMR CDCl$_3$ 250 MHz 2.79 (m) and 2.94 (m): the CH$_2$'s; 7.05 to 7.25: the aromatics; 9.82 (t): CHO.

EXAMPLE 11

11,12-dideoxy-3-de-[(2,6-dideoxy-3-C-methyl-3-O-methyl-α-ribohexopyranosyl)-oxy)-6-O-methyl-3-oxo-12,11-(oxycarbonyl-(2-(3-(4-quinolinyl)-2-propyl)-hydrazono)]-erythromycin Stage A: 11,12-dideoxy 3-de-[(2,6-dideoxy-3-C-methyl-3-O-methyl-αL-ribohexopyranosyl)-oxy)-6-O-methyl-3-oxo-12,11-(oxycarbonyl(hydrazono)]-erythromycin isomer 10(R) and corresponding isomer 10(S)

17.65 g of 11-deoxy-10,11-didehydro-3-de(2,6-dideoxy-3-C-methyl-3-O-methyl-α-L-ribohexopyranosyl)-oxy)-12-O-((1H-imidazol-1-yl)-carbonyl)-6-O-methyl-3-oxo-erythromycin-2'-acetate were dissolved in 176 ml of methyl cyanide and 4.07 g of caesium carbonate and 25.5 ml of hydrazine hydrate were added thereto. After heating for 10 minutes at 85° C., the solvent was evaporated under reduced pressure at 40° C. Extraction was carried out with methylene chloride, followed by washing with water and drying. The solvent was evaporated and the residue was taken up in methanol. The precipitate was separated and dried at 50° C. under reduced pressure to obtain 6.04 g of product. The mother liquors were concentrated to dryness and the residue was chromatographed on silica (eluant: isopropyl ether-methanol-triethylamine 80-10-10) to obtain 0.83 g of isomer A with a R$_f$=0.4 and 2.65 g of isomer B with a R$_f$=0.2.

Stage B: 11,12-dideoxy-3-de-[(2,6-dideoxy-3-C-methyl-3-O-methyl-α-L-ribohexopyranosyl)-oxy)-6-O-methyl-3-oxo-12,11(oxycarbonyl-(2-(3-(4-quinolinyl)-2-propyl)-hydrazono)]-erythromycin 13 g of the product of Stage A and 4.66 g of 4-quinoline-propanal were suspended in 130 ml of methanol and 4.8 ml of acetic acid were added. The mixture was stirred for 20 hours at ambient temperature and then 5.3 g of sodium cyanoborohydride were added. The mixture was stirred for 4 hours and the methanol was eliminated under reduced pressure. Extraction was carried out with ethyl acetate, followed by washing with an aqueous solution of N sodium hydroxide, then with water. The solvent was evaporated from the organic phase and the residue was chromatographed on silica (eluant: ethyl acetate-triethylamine 97-3) to obtain 12.7 g of product with a R$_f$=0.15. After another chromatography on silica (eluant: methylene chloride-methanol 95-5 then 85-15) and crystallization from isopropyl ether, the pure product melting at 183° C. and with analyses identical to those of Example 5 was obtained.

PREPARATION OF: 4-quinoline-propanal

Stage A: 2-(4-quinolinyl-ethenyl)-1,3-dioxolane 3.15 g of 4-quinoline-carboxaldehyde and 8.6 g of [1,3-(dioxalan-2-yl)-methyl]-triphenylphosphonium-bromide were suspended in 40 ml of tetrahydrofuran and after the suspension was cooled to −30° C., 2.5 g of potassium terbutylate were added. The mixture was stirred for one hour and then was allowed to return to ambient temperature with stirring for 3 hours. The mixture was poured into a water/ice mixture and extraction was carried out with methylene chloride, followed by washing with water and drying. The solvent was evaporated under reduced pressure and the residue was taken up in an ethyl ether-pentane mixture 3-7. The mixture was stirred for 2 hours, followed by filtration, and the solvent was evaporated from the filtrate to obtain 3.99 g of the expected product.

Stage B: 2-[2-(4-quinolinyl)-ethyl]-1,3-dioxolane 4.3 g of the product of Stage A were dissolved in 40 ml of methanol and 0.215 g of activated charcoal with 10% palladium were added. Hydrogenation was carried out for 2 hours under a pressure of 1500 mbars. After filtration and rinsing with methanol, the solvent was evaporated to obtain 4.2 g of the expected product which was used as is for the following stage.

Stare C: 4-quinoline-propanal 4.2 g of the product of Stage B were dissolved in 70 ml of acetone and 70 ml of 2N hydrochloric acid were added. Heating was carried out for 6 hours at 40° C. and the acetone was eliminated under reduced pressure. Extraction was carried out with ethyl acetate, followed by washing with water. The aqueous phase was adjusted to a pH of 9 with an aqueous solution of ammonium hydroxide. Extraction was carried out with ethyl acetate and the combined organic phases were dried and the solvent was evaporated. After chromatography on silica (eluant: ethyl acetate-cyclohexane 6-4), 1.36 g of the expected product were obtained.

EXAMPLE 12

11,12-dideoxy-3-de-[(2,6-dideoxy-3-C-methyl-3-O-methyl α-L-ribohexopyranosyl)-oxy)-6-O-methyl-3-oxo-12,11-(oxycarbonyl-2-(3-(7-methoxy-4-quinolinyl)-propyl)-hydrazono)]-erythromycin 299 mg of 7-methoxy-4-quinoline and 313.9 mg of product A of Example 1 and 120 µl of acetic acid were dissolved in 2 ml of methanol and the mixture was stirred for 2 hours 15 minutes at ambient temperature. Then 62.84 g of sodium cyanoborohydride were added and the mixture was stirred for 20 hours at ambient temperature. The reaction medium was poured into 50 ml of ethyl acetate, washed with 15 ml of N sodium hydroxide, then with water and dried. The solvent was evaporated under reduced pressure to obtain 549 mg of product which was purified by chromatography on silica (eluant: isopropyl ether-methanol-triethylamine 80-10-10), then (chloroform-methanol-ammonium hydroxide 96-4-0.4) to obtain 37.2 mg of the expected product with a R$_f$=0.2.

|  | C | H | N |
|---|---|---|---|
| % calculated | 63.84 | 8.04 | 6.77 |
| % found | 63.8 | 8.1 | 6.6 |

NMR CDCl$_3$ 300 MHz 3.74 (s): H$_{11}$; 3.17 (m): NH—CH$_2$; 3.95 (s): OCH$_3$ of the quinoline; 7.16–7.41 (d)–8.00 (d)–8.70 (d): H quinoline; 3.87 (q): H$_2$; 2.65 (s): 6-OCH$_3$; 2.65 (m): H$_8$; 0.82 (t): CH$_3$—CH$_2$.

PREPARATION OF: 7-methoxy-4-quinoline-propanal

Stage A: 2-[(7-methoxy-4-quinolinyl)-ethenyl]-1,3-dioxolane

Using the procedure of the preparation of Example 11, Stage A 787 mg of 7-methoxy-4-quinoline-carboxaldehyde were reacted to obtain 2.61 g of product which was chromatographed on silica (eluant: chloroform-ethyl acetate 7-3) to obtain 931 mg of the expected product.

Stage B: 2-[2-(7-methoxy-4-quinoline)-ethyl]-1,3-dioxolane

Using the procedure of the preparation of Example 11 Stage B, 931 mg of the product of Stage A were reacted to obtain 869 mg of the expected product.

Stage C: 2-(7-methoxy-4-quinoline)-propanal

Using the procedure of the preparation of Example 11 Stage C, 845 mg of the product of Stage B were reacted to obtain 310 mg of the expected product with a R$_f$=0.15.

EXAMPLE 13

11,12-dideoxy-3-de-[(2,6-dideoxy-3-C-methyl-3-O-methyl-α-L-ribohexopyranosyl)oxy)-6-O-methyl-3-oxo-12,11-(oxycarbonyl-2-(3-(2-(3-pyridinyl-4-thiazolyl)-propyl)-hydrazono)]-erythromycin Using the procedure of Example 12, 158 mg of 2-(3-pyridinyl)-4-thiazole-propanal, 370 mg of product A of Example 1 and 70 µl of acetic acid in 3.7 ml of methanol were admixed and then after stirring for 4 hours at ambient temperature. 75 mg of sodium cyanoborohydride were added. After 16 hours of stirring at ambient temperature, another 16 mg of aldehyde and 20 mg of reducing agent were added and stirring was continued for 3 hours. Water and ethyl acetate were added. followed by alkalinizing to a pH of 9 using ammonium hydroxide. The organic phase was washed with water, dried and the solvent was evaporated under reduced pressure. After chromatography on silica (eluant: isopropyl ether-methanol-triethylamine 80-10-10), 203 mg of the expected product were obtained. 3.13 (m): $H_{10}$; 3.74 (s) : $H_{11}$; 7.05 (s): $H_5$ thiazole; 7.37 (dd)-8.24 (ddd)-8.62 (dd)-9.13 (dd) : pyridine; 3.86 (q) : $H_2$; 2.65 (s) : 6-$OCH_3$; 2.66 (m); $H_8$; 0.85 (t): $CH_3$—$CH_2$.

PREPARATION OF: 2-(3-pyridinyl)-4-thiazole-propanal

Stage A: [[2-(3-pyridinyl)-4-thiazolyl]-ethenyl]-1,3-dioxolane

Using the procedure of the preparation of Example 11, Stage A. 2.6 g of 2-(3-pyridinyl)-4-thiazolyl-carboxaldehyde were reacted to obtain after chromatography on silica (eluant: ethyl acetate-hexane 2-1) 4.8 g of the expected product with a $R_f$=0.35 which was used as is for the following stage.

Stage B: 2-[2-((3-pyridinyl)-4-thiazolyl)-ethyl]-1,3-dioxolane

Using the procedure of the preparation of Example 11, Stage B, 4.8 g of the product of Stage A were reacted to obtain after chromatographing the residue on silica (eluant: ethyl acetate-cyclohexane 2-1) 1.4 g of the expected product.

Stage C: 2-(3-pyridinyl)-4-thiazolyl-propanal

Using the procedure of the preparation of Example 11, Stage C, 1.2 g of the product of Stage B were reacted to obtain after chromatography on silica (eluant: ethyl acetate-hexane 2-1) 468 mg of the expected product.

Using the procedure of the previous examples and starting with the compound of Example 1 and the appropriate aldehyde, the following products were prepared:

EXAMPLE 14

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-2-(3-(1H-imidazol-1-yl)-propyl)-hydrazono)]-erythromycin NMR ($CDCl_3$) 300 MHz: 0.83 (t): $CH_3$—$CH_2$; 1.08 (d)-1.17 (d)-1.25 (d)-1.3 (d)-1.35 (d): the $CH_3$—CH's; 1.3 (s)-1.47 (s): 6 and 12 Me; 2.12 (m): $CH_2$—$CH_2$—$CH_2$; 2.27 (s): $N(Me)_2$; 2.45 (m): H'$_3$; 2.59 (s): 6-OMe; 3.05 (m): $H_4$; 2.6 to 3.2: H'$_2$, $H_{10}$: $H_8$ and $CH_2NH$; 3.53 (m): H'$_5$; 3.72 (s) $H_{11}$; 3.85 (q) $H_2$; 4.27: H'$_1$ and $H_5$; 4.63 (m): $CH_2$—N; 4.99 (dd) $H_{13}$; 5.46 (t): NH—$CH_2$; 7.10–7.64–7.66–7.97: aromatics.

EXAMPLE 15

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-2-(3-(3H-imidazo-(4,5-b)pyridin-3-yl)-propyl)-hydrazono)]erythromycin.

NMR ($CDCl_3$) 300 MHz: 0.85 (t): $CH_3$—$CH_2$; 1.09–1.19 (d)-1.25 (d)-1.31 (d)-1.34 (d): the $CH_3CH$'s; 1.33 and 1.48: 6 and 12 Me; 1.57 and 1.96: $CH_2$ in position 14; 1.66 and 1.87: $CH_2$ in position 7; 2.05 and 2.18: $CH_2$—$CH_2$—$CH_2$; 2.26 (s) : $N(CH_3)_2$; 2.44 (m) : H'$_3$; 2.6 (s) : 6-$OCH_3$; 2.66 (m) : $H_8$; 2.70 to 2.85: $CH_2NH$; 3.04 (m): $H_4$; 3.18: $H_2H_{10}$; 3.70 (s): $H_{11}$; 3.85 (q): $H_2$; 4.27: H'$_1$ and $H_5$; 4.42 to 4.70: $CH_2$—N; 4.97 (dd) : $H_{13}$; 5.56 (t): NH; 8.22 (dd)-8.05 (d)-8.28 (s)-8.38 (d): aromatics.

EXAMPLE 16

11,12-dideoxy-3-de-[(2,6-dideoxy-3-C-methyl-3-O-methyl-α-L-ribohexopyranosyl)-oxy-6-O-methyl-3-oxo-12,11-(oxycarbonyl-2-(3-(1,1'-biphenyl-4-yl)-propyl)-hydrazono)]-erythromycin NMR ($CDCl_3$) 300 MHz: 0.87 (t): $CH_3$—$CH_2$; 1.08 (d)-1.18 (d)-1.23 (d)-1.32 (d)-1.38 (d): the $CH_3$—CH's; 1.34 (s) and 1.48 (s) : 6 and 12 Me; 2.26 (s): $N(CH_3)_2$; 2.44 (m): H'$_3$; 2.65 (s): 6-$OCH_3$; 2.65 (m) $H_8$; 2.77 (in) $CH_2$—Ar; 2.85 (t): $CH_2NH$; 3.07 (ml): $H_4$; 3.18 (m) : H'$_2$, $H_{10}$; 3.25 (m): H'$_5$; 3.76 (s): $H_{11}$; 3.87 (q): $H_2$; 4.27: H'$_1$ and $H_5$; 5.04 (dd): $H_{13}$; 5.37 (t): NH—$CH_2$; 7.25 to 7.6: aromatics.

EXAMPLE 17

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-2-(3-(2-phenyl-4-thiazolyl)-propyl)-hydrazono)]-erythromycin NMR ($CDCl_3$) 300 MHz: 0.86 (t): $CH_3$—$CH_2$; 1.07 (d)-1.19 (d)-1.24 (d)-1.31 (d)-1.35 (d): the $CH_3$—CH; 1.32 (s)-1.48 (s) : 6-$CH_3$ and 12-$CH_3$; 2.26 (s): $N(CH_3)_2$; 2.65 (s): 6-$OCH_3$: 2.45 (m): H'$_3$; 2.65 (m): $H_8$; 2.8 to 3.25 (m): $H_4$, $H_{10}$, H'$_2$, $CH_2$—Ar and $CH_2N$; 3.53 (): H'$_5$; 3.76 (): $H_{11}$; 3.86 (q): $H_2$; 4.27 (d): H'$_1$ and $H_5$; 5.04 (dd): $H_{13}$; 5.36 (t): NH; 6.96–7.40–7.93: aromatics.

EXAMPLE 18

11,12-dideoxy 3-de-[(2,6-dideoxy-3-C-methyl-3-O-methyl-α-L-ribohexopyranosyl)-oxy)-6-O-methyl-3-oxo-12,11-(oxycarbonyl-2-(3-(5-phenyl-1,2,4-thiadiazol-3-yl)-propyl)-hydrazono)]erythromycin NMR ($CDCl_3$) 300 MHz: 0.87 (t): $CH_3$—$CH_2$; 1.33 and 1.47: 6 and 12 Me; 2.17 (m): $CH_2$—$CH_2$—$CH_2$; 2.26 (s): $N(CH_3)_2$; 2.67 (s): 6-$OCH_3$; 2.67 (s): $H_8$; 3.76 (s): $H_{11}$; 3.85 (q): $H_2$; 5.06 (dd): $H_{13}$; 5.39 (t): NH—$CH_2$; 7.49–7.94: aromatics.

EXAMPLE 19

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-2-(3-(4-(4-chlorophenyl-1H-imidazol-1-yl)-propyl)-hydrazono)]-erythromycin.

EXAMPLE 20

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-2-(3-(6-methoxy-4-quinolinyl)-propyl)-hydrazono)]-erythromycin Using the procedure of Example 12, the expected product was obtained.

NMR $CDCl_3$ 300 MHz 3.74 (s) : $H_{11}$; 5.52 (tl) : NH—$CH_2$; 3,98 (s): $OCH_3$ of quinoline; 7,25–7.35 (d)-7,99 (d)-8,65 (d) H quinoline; 3,87 (q) : $H_2$; 2,64 (s): 6-$OCH_3$; 2,64 (m): $H_8$; 5,02 (dd): $H_{13}$.

Using the said procedure above, the compounds of formula I were prepared in which

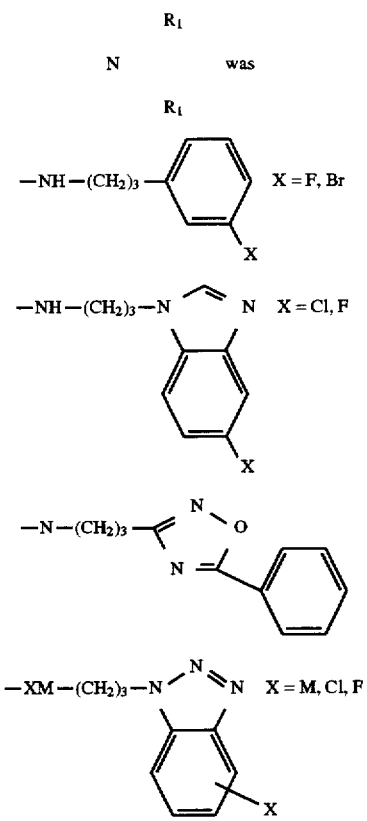

EXAMPLE OF PHARMACEUTICAL COMPOSITION

Tablets were prepared containing 150 mg of the product of Example 5 and sufficient Excipient of starch, talc, and magnesium stearate to obtain tablets of 1 g.

PHARMACOLOGICAL STUDY

Method of dilutions in liquid media

A series of tubes were prepared into which an equal amount of sterile nutritive medium was distributed and increasing amounts of the product being studied were distributed into each tube. Then, each tube was seeded with a bacterial strain and after incubation for twenty-four hours in an oven at 37° C., the growth inhibition was evaluated by trans-illumination which allowed the minimal inhibiting concentrations (M.I.C.) to be determined expressed in mnicrograms/ml. The following results were obtained with the product of Example 5: (reading after 24 hours)

| GRAM+ bacterial strains | |
|---|---|
| *Staphylococcus aureus* 011UC4 | 0.02 |
| *Staphylococcus aureus* 011G025I | 0.08 |
| *Staphylococcus epidermidis* 012GO11I | 0.04 |
| *Streptococcus pyrogenes* group A 02A1UC1 | ≦0.02 |
| *Streptococcus agalactiae* group B 02B1HT1 | ≦0.02 |
| *Streptococcus faecalis* goup D 02D2UC1 | ≦0.02 |
| *Streptococcus faecium* | ≦0.02 |

| GRAM+ bacterial strains | |
|---|---|
| group D 02D3HT1 *Streptococcus sp* group G 02G0GR5 | ≦0.02 |
| *Streptococcus mitis* 02mitCB1 | ≦0.02 |
| *Streptococcus agalactiae* group B 02B1SJ1 | ≦0.02 |
| *Streptococcus pneumoniae* 032UC1 | ≦0.02 |
| *Streptococcus pneumoniae* 030SJ5 | ≦0.02 |

Moreover, the product of Example 5 demonstrated a useful activity on the GRAM bacterial strains Haemophilus Influenzae 351HT3, 351CB12, 351CA1 and 351GR6.

The compounds of Examples 12 and 13 have equally demonstrated an excellent activity on the gram (−) and gram (+) bacterial strains. Operating as indicated previously, the following results were obtained with the compounds of examples 12 and 13 (reading after 24 hours).

| GRAM+ bacterial strains | Ex. 12 | Ex. 13 |
|---|---|---|
| *Staphylococcus aureus* 011UC4 | 0,08 | 0,04 |
| *Staphylococcus aureus* 011G025I | 0,08 | 0,15 |
| *Staphylococcus epidermidis* 012GO11I | 0,04 | 0,04 |
| *Streptococcus pyogenes* 02A1UC1 | ≦0,02 | ≦0,02 |
| *Streptococcus agalactiae* 02B1HT1 | ≦0,02 | ≦0,02 |
| *Streptococcus faecalis* 02D2UC1 | ≦0,02 | ≦0,02 |
| *Streptococcus faecium* 02D3HT1 | ≦0,02 | ≦0,02 |
| *Streptococcus pneumoniae* 032UC1 | 0,04 | ≦0,02 |
| *Streptococcus pneumoniae* 03OSJ5I | ≦0,02 | ≦0,02 |
| *Streptococcus pneumoniae* 030CR18C | 0,6 | 0,6 |
| *Haemophilus inflienzae* 351HT3 | 1,2 | 0,6 |
| *Haemophilus inflienzae* 351CB12 | 1,2 | 1,2 |

Various modifications of the products and method of the invention may be made without departing from the spirit or scope thereof and it is to be understood that the invention is intended to be limited only as defined in the appended claims.

What is claimed is:

1. A compound selected from the group consisting of
3-imidazolyl-propanal,
2-phenyl-5-thiazole-propanal,
3-(4-phenyl-1H-imidazol-1-yl)-propanal,
3-(3-phenyl-1,2,4-oxadiazol-5-yl)-propanal,
3-(2-chlorophenyl)-propanal,
4-quinoline-propanal,
7-methoxy-4-quinoline-propanal and
2-(3-pyridinyl)-4-thiazole-propanal.

* * * * *